United States Patent [19]
Messerschmidt et al.

[11] Patent Number: 4,661,706
[45] Date of Patent: Apr. 28, 1987

[54] BLOCKER DEVICE FOR ELIMINATING SPECULAR REFLECTANCE FROM A DIFFUSE REFLECTION SPECTRUM

[75] Inventors: Robert G. Messerschmidt, Westport; Donald W. Sting, New Canaan, both of Conn.

[73] Assignee: Spectra-Tech Inc., Stamford, Conn.

[21] Appl. No.: 705,201

[22] Filed: Feb. 25, 1985

[51] Int. Cl.$^4$ ............................................. G01J 1/00
[52] U.S. Cl. .................................. 250/341; 250/353; 250/372
[58] Field of Search ................ 250/338 R, 341, 353, 250/372, 336.1, 461.1; 350/266, 268

[56] References Cited
U.S. PATENT DOCUMENTS

| | | | |
|---|---|---|---|
| 3,177,757 | 4/1965 | Polanyi . | |
| 3,564,262 | 2/1971 | Hach | 250/218 |
| 3,854,045 | 12/1974 | Breuer et al. | 250/341 |
| 3,947,088 | 3/1976 | French | 350/96 C |
| 3,962,581 | 6/1976 | Zimmerman | 250/341 |
| 4,029,391 | 6/1977 | French | 350/96 C |
| 4,353,618 | 10/1982 | Hagner | 350/91 |
| 4,473,295 | 9/1984 | Doyle | 356/244 |

OTHER PUBLICATIONS

Griffiths, P. R. et al., "Mid—Infrared Spectrometry of Powdered Samples," *Advances in Infrared and Raman Spectroscopy*, vol. 9, Chap. 2.

Primary Examiner—Janice A. Howell
Attorney, Agent, or Firm—Bacon & Thomas

[57] ABSTRACT

Diffuse reflectance spectra may be obtained that are free from the distortions caused by specular reflections by using an apparatus and method for physically blocking out specularly reflected energy. The apparatus consists of a blocker that is positioned substantially in contact with the surface of the sample at the region wherein an input beam of energy is focused on the sample. Specularly reflected energy that would otherwise be reflected to a detector is physically blocked by the blocker. That part of the input energy beam that penetrates into the sample is diffusely reflected. Part of the diffusely reflected energy passes under the blocker where it is collected and focused on the detector. The blocker is found to have particular application in the field of infrared spectroscopy of inorganic compounds, particularly compounds having a powdered structure.

20 Claims, 20 Drawing Figures

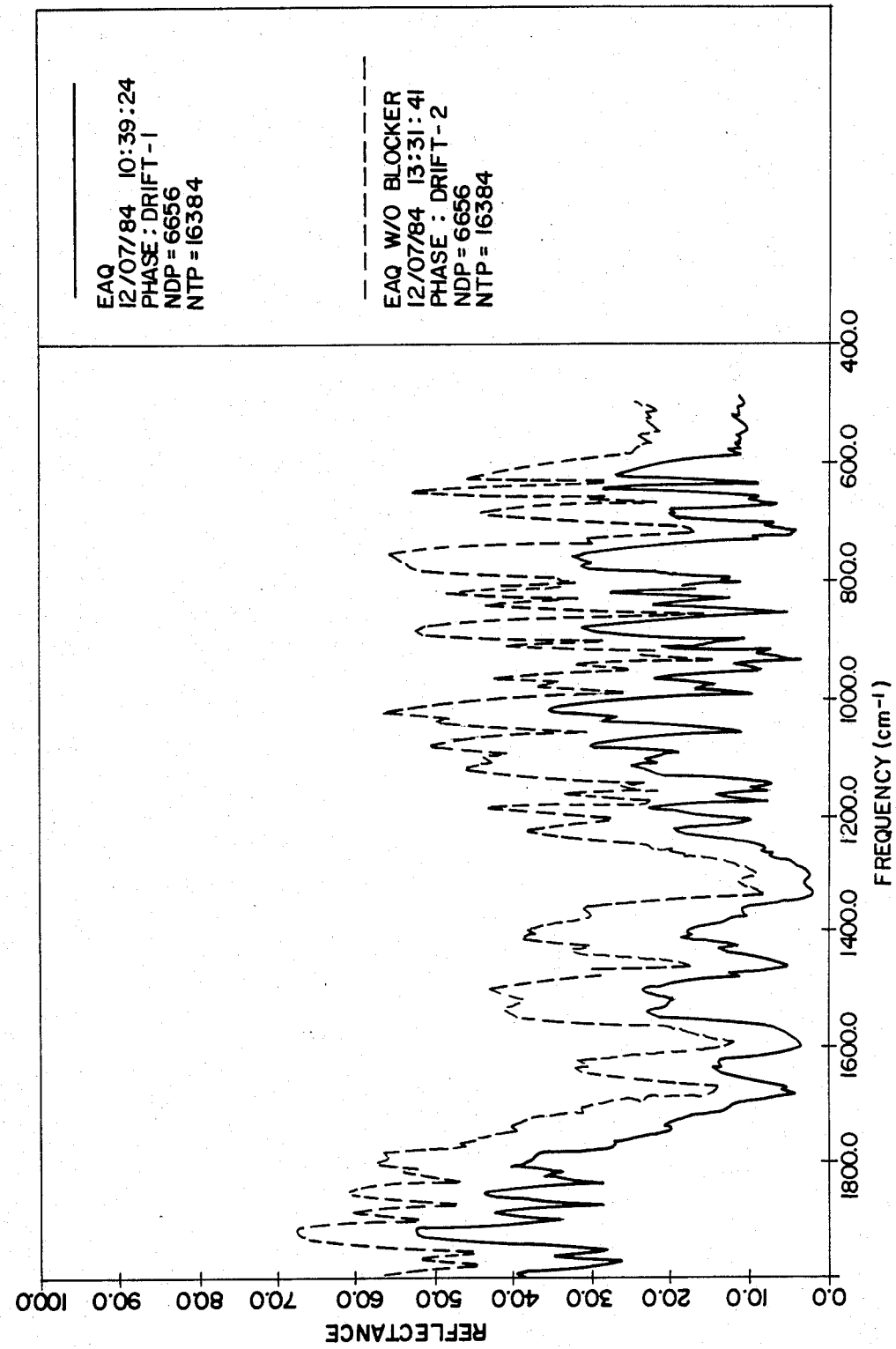

BLOCKER DEVICE FOR ELIMINATING SPECULAR REFLECTANCE FROM A DIFFUSE REFLECTION SPECTRUM

FIELD OF THE INVENTION

This invention deals with a method and apparatus for obtaining diffuse reflectance spectra, wherein the specular component of the diffuse spectra is substantially eliminated. Distortions in the diffuse reflectance spectra caused by the specular component are thus eliminated.

BACKGROUND OF THE INVENTION

It is known that particular compounds possess unique spectral signatures. One method to obtain a spectrum indicative of a particular compound is transmission spectroscopy. A transmission spectrum can be obtained by transmitting an energy beam of known intensity and frequency through an at least partially transmissive sample and recording the intensity of the energy transmitted through the sample at various incident wavelengths. This method works quite well for a wide range of compounds having known transmission spectra. More recent technology for obtaining infrared spectra uses interferometers and computers in what is commonly called Fourier Transform Infrared (FTIR) spectroscopy. This technology has proved to have significant advantages over prior art methods of obtaining infrared spectra. A transmission spectrum cannot, generally, be obtained for a compound composed of powder grains or small size granules, particularly when the powder is substantially opaque to the frequencies of the incident energy at common granule thickness. One solution in such an instance is to embed the powder or granules in a matrix not having spectral features in the frequency range of the incident energy beam. This method only works so long as a suitable matrix compound can be found and the powder or granules are not so opaque as to absorb all input energy when the matrix contains a sufficient density of the sample to produce a meaningful spectrum from the sample.

Another solution to the problem associated with powders or granular samples is to obtain a diffuse reflectance spectrum of the sample. A diffuse reflectance spectrum is obtained by directing an input energy beam onto the surface of the sample, collecting the diffusely reflected energy from the sample and directing that energy to a detector. Diffusely reflected energy is energy which is defined to be reflected from below the surface of the sample. The energy diffusely reflected from a sample does not have a preferred direction of reflection, i.e., the diffusely reflected energy leaves the sample surface in a hemispherical pattern. The diffusively reflected energy has spectral characteristics that uniquely identify the sample compounds and correspond to the spectrum obtained by transmissive means.

In addition to diffuse reflection, however, an energy beam directed against the surface of a sample produces specular reflection. Specular reflection is defined to be incident energy that is reflected from a surface of a sample as opposed to diffusely reflected energy which is energy reflected from below the sample surface. Specular reflectance obeys Snell's Law which states that the angle of incidence of the input energy beam equals the angle of reflectance. In other words, energy that is specularly reflected behaves as light reflected from a mirror. Thus, if all the crystals on the surface of a powder sample were oriented so as to present a homogenous reflective face to the incident energy that was parallel to the plane of the sample, the incident energy would reflect off the surface of the sample according to Snell's Law. However, the reflecting surfaces of individual crystals on the surface of a powder sample are somewhat randomly oriented and, therefore, scatter the incident energy over an entire hemisphere as is the case for diffuse reflection. Our experiments and those of others have shown that the crystals on the surface of a sample may often be oriented so as to produce a preferred direction of reflection. Nevertheless, some of the incident energy beam is nearly always specularly reflected over all angles of reflection. A detailed discussion of the spectrometry of powdered samples is found in Griffiths et al, *Advance in Infrared and Raman Spectroscopy*, Vol. 9, Chapter 2, (Heyden, London 1981) the disclosure of which is hereby incorporated by reference.

Conventional analysis of diffuse reflectance spectra employs the Kubelka-Munk function. The Kubelka-Munk function states that the strength of an absorption feature in a diffuse reflectance spectrum is linearly related to the concentration of the compound producing the spectral feature. The function involves a relationship between an absorption coefficient, a scattering coefficient and the ratio of the diffuse reflectance from a sample and that of a non-absorbing powder reference. The function assumes that the sample extends to an infinite optical depth, i.e., that depth at which the addition of more sample material to the bottom of the sample does not change the amount of energy diffusely reflected. In theory, the Kubelka-Munk function should enable a spectrum obtained by diffuse reflectance to be compared to a spectrum obtained by transmissive means. The transmission spectrum for many compounds is known. Hence, the ability to identify a compound from its diffuse reflectance spectrum given a known transmission spectrum enables diffuse reflectance spectroscopy to accurately identify trace elements present in powdered samples that do not lend themselves to direct transmission spectroscopy. A specific example of the application of diffuse reflection spectroscopy is in quality control of pharmaceutical tablets to eliminate the need to grind up the tablets and embed them in a non-absorbtive matrix. Moreover, it is believed that it will be possible to apply spectral subtraction routines commonly used in absorption spectroscopy to diffuse reflectance measurements to identify trace elements in the sample and to accurately establish their concentration in the sample.

The linearity of the Kubelka-Munk relationship for the strength of an absorption feature with concentration, however, breaks down for experimental conditions involving specular reflectance. Specular reflectance alters a diffuse spectrum in a complex manner which is not well understood. The spectrum produced from specular reflection is a complex, nonlinear function dependent on wavelength, particle size, index of refraction of the particular materials present in the sample, the presence or absence of an absorption band in the surface material and the strength of the band. Moreover, the spectrum obtained from a diffusely reflecting sample may change by simply changing the orientation of the sample or by merely brushing the surface of the sample. At best, specular reflectance convolves the Kubelka-Munk relationship with another slightly nonlinear function. In certain instances, such as for inorganic samples at infrared energies, the effect of specular reflectance is more severe, producing complete inversion of spectral bands, referred to as a reststrahlen bands, or derivative shaped spectral peaks. The effect of specular reflectance is to make quantitative analysis of the diffuse spectrum an extremely complicated and error prone undertaking. In many cases, qualitative interpretation of the diffuse reflectance spectrum convolved with specular reflection produces erroneous information as to the composition or concentration of a sample. Therefore, to obtain accurate and useful information, it is highly desirable to eliminate the specular reflectance component from the diffuse reflectance spectra.

As noted above, specular reflection behaves like a mirror with incident energy reflected from a powder surface according to Snell's Law without penetrating into the sample. Any specular component should ideally leave the sample with a smaller angular spread than the diffuse component. Although powdered or granular surfaces adhere to Snell's Law for individual granules, the reflection properties of the aggregate surface can be quite different. However, surface preparation techniques could be used to orient the surface granules so that Snell's Law reasonably approximates the reflectance off the surface. Therefore, certain collection angles could, in principle, contain a pure diffuse reflection spectrum, and rotation of the collection mirror away from a symmetrical collection angle would eliminate the specular component of the energy reflected back from the sample.

Our experiments have shown that specular reflection may indeed have a preferential orientation along the direction predicated by Snell's Law. However, some specularly reflected energy has been found at all angles of reflection. The magnitude of the specular component over a given angle is a function of the manner in which the sample cup is filled and prepared. Standard practice in examining a powder sample has included drawing a straight edge across the powder surface prior to taking a spectrum. This manner of preparing the surface appears to be highly effective at orienting individual crystals and increases the likelihood that a comparable diffuse reflectance spectrum may be obtained from samples that are identical in composition. However, orienting the surface crystals increases the magnitude of energy that is specularly reflected towards the detector without confining the specular reflection to a particular angle. Thus, while this method might improve repeatability inherent distortions are also repeated.

Roughening the surface of the sample reduces the total amount of specular reflectance directed towards the collector. The roughening may take the form of drawing a camel hair brush over the sample or placing a piece of adhesive tape in light contact with the top of the sample and subsequently removing the tape. However, roughening the surface to the same degree is difficult and does not completely eliminate the specular component. Indeed, a completely roughened surface having crystals randomly oriented produces specular reflection over all angles of reflection without a known preferred orientation.

Another method of attempting to eliminate the specular component from a diffuse reflectance spectrum involves diluting the specularly reflective sample in a matrix having no spectral features a the wavelength of the incident energy and no distorted specular reflectance properties. This method is subject to the limitation of being able to find an inert matrix material that does not have absorptive or reflective properties in the given range of energy. The method often requires destroying the sample so that it can be mixed with the matrix material.

The foregoing discussion demonstrates an acknowledged need for some means by which to eliminate specular reflection from diffuse reflectance spectra. We have found a particular need for eliminating the distortion caused by specular reflectance in obtaining diffuse reflectance spectra of inorganic compounds. This is because certain inorganic compounds are not suited for infrared analysis by transmssive means and may not be analyzed with any of the foregoing methods due to the extreme distortion of their diffuse reflectance spectrum caused by their inherent specular properties. More generally, there has not hitherto been a simple means for quickly and economically obtaining an undistorted diffuse reflectance spectrum of any sample having specular reflective properties that is not subject to random distortions caused by the orientation of granules on the surface of the sample.

SUMMARY OF THE INVENTION

The invention is directed to a method and apparatus for eliminating specular reflectance from the diffuse reflectance spectrum of a reflecting sample. In most general terms, the method comprises directing energy onto a surface of a sample, positioning a blocking element at the surface of the sample to separate specularly reflected energy from diffusely reflected energy so that the diffusely reflected energy can be separately collected. The apparatus of the invention includes means for providing an input beam of energy, means for focusing and collecting energy onto and from a reference sample and means for eliminating substantially all specularly reflected energy from the energy collected from the sample. More specifically, the invention utilizes a thin blade as the blocking element (also referred to as the blocker) placed in substantial contact with the surface of the sample at the intersection of the surface with the incident energy beam to substantially eliminate the specular reflection from the diffusely reflected energy beam.

BRIEF DESCRIPTION OF THE DRAWINGS

FIG. 14 shows comparison spectra with and without the blocker of the present invention for ethylanthroquinone showing how the blocker does not have a substantial effect on the spectrum of a compound lacking a large degree of specular reflectance.

DETAILED DESCRIPTION OF THE PREFERRED EMBODIMENTS

Figure 1:
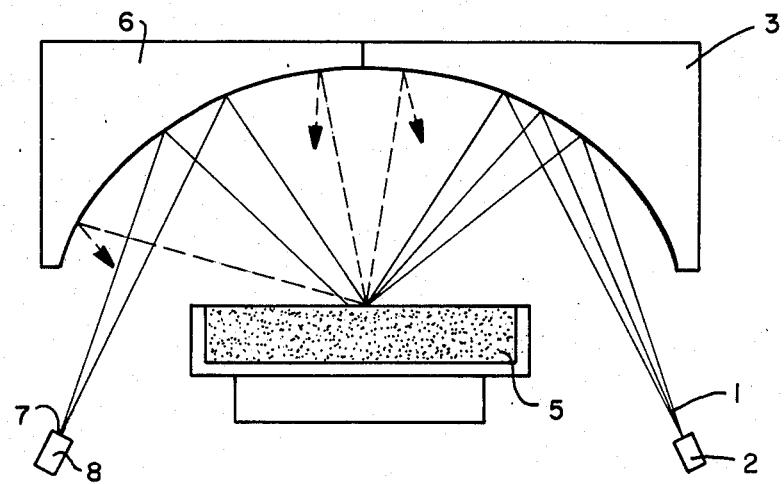
FIG. 1 is a schematic sideview illustrating the light path taken by light impinging upon a diffusely and specularly reflecting sample.

FIG. 1 shows the effect of diffuse scattering from a sample. An input beam 1 emitted from source 2 reflects off a focusing ellipsoid mirror 3 onto a sample 5. While infrared light is the most common energy for use in the invention, energy of other wavelengths may be suitable. Reflected energy bounces off sample 5 onto an output half of the ellipsoid mirror 6 to focus 7 where it is targeted on the detector 8. At most, one-half the input energy reaches the output half of the ellipsoid mirror because the diffusely reflected light from the sample is reflected over all angles.

Figure 2:
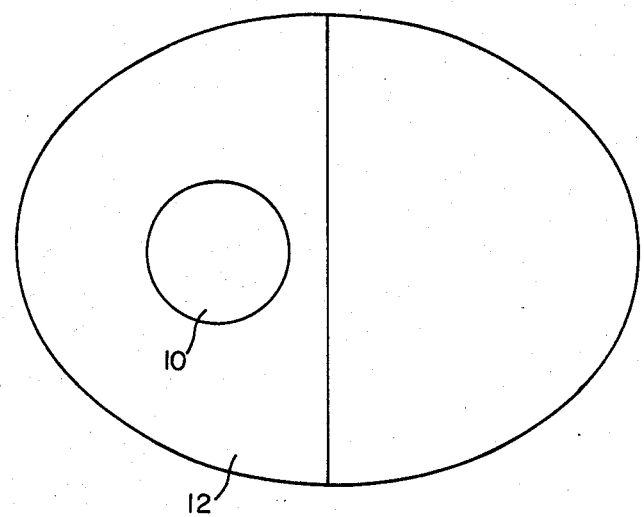
FIG. 2 is a bottom view of the focusing ellipsoid in FIG. 1.

If sample 5 is replaced with a mirror, all the reflective energy will fall on region 10 as shown in FIG. 2. Thus, specularly reflected energy from a sample would, under ideal conditions, obey Snells' Law and fall only on region 10. However, in practice, specularly reflected energy falls on both regions 10 and 12 of ellipsoid mirror 6 due to random orientation of the crystals on the surface of the sample.

Figure 3A:
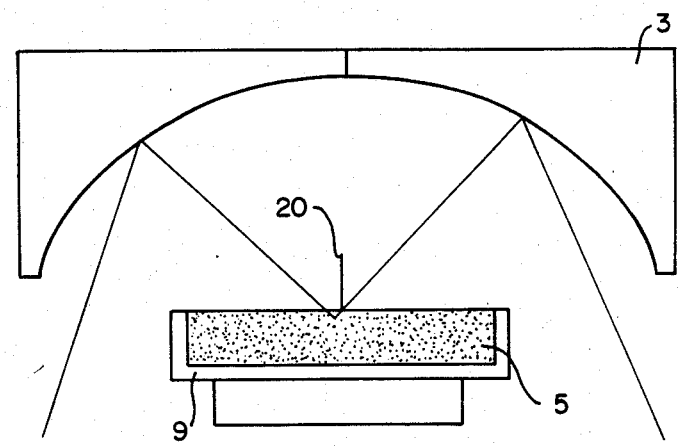
FIGS. 3A and 3B schematically shows a specular blocker device according to the present invention in use in conjunction with the apparatus shown in FIG. 1.

In FIG. 3A blocker 20 according to the present invention is positioned over the sample 5 which is contained in cup 9. In a preferred embodiment of the invention, the blocker is a straight edged piece of metal, although any material that is opaque to the incident energy may suffice. The blocker should be made from material that does not have reflective spectral features in the energy range of the input beam. This requirement is satisfied for the infrared region by gold plating the blocker because gold is completely reflective in the infrared region. A blocker coated with a material that is completely absorbent of the incident energy could also be employed.

Blocker 20 is positioned relative to sample 5 and the focus of input beam 1 reflected off focusing ellipsoid mirror 3 to eliminate the specular component of reflected energy from sample 5 by physically blocking the energy reflected from the surface of the sample. Any means for holding the blocker in position can be employed. A preferred means is achieved by mounting the blocker on a pivoting arm which allows it to be moved into position during operation and pivotally out of position to facilitate replacement of the sample. It is important that the blocker contacts the surface of the sample so as to prevent specularly reflected input radiation from leaking under the blocker and reaching the output half of the ellipsoid 6. The blocker must be separated from the surface by less than a fraction of a wavelength of the incident energy. If the blocker is to prevent specularly reflected input energy from leaking under a bottom edge of the blocker the physical contact of a metal blocker with the surface of the sample may also advantageously eliminate light waves propagating along the surface of the sample that may form a component of the specularly reflected light.

Figure 3B:
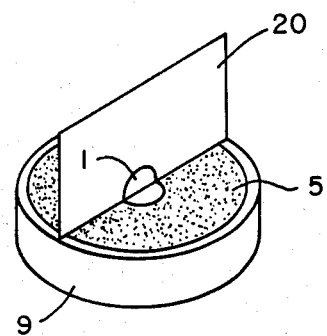

The intersection of the blocker and the surface of the sample should be located on the sample at the focus of the input energy being reflected off focusing ellipsoid mirror 3. As shown in FIG. 3B, the blocker splits the image focal plane of the input beam on the surface of sample 5.

Figure 4A:
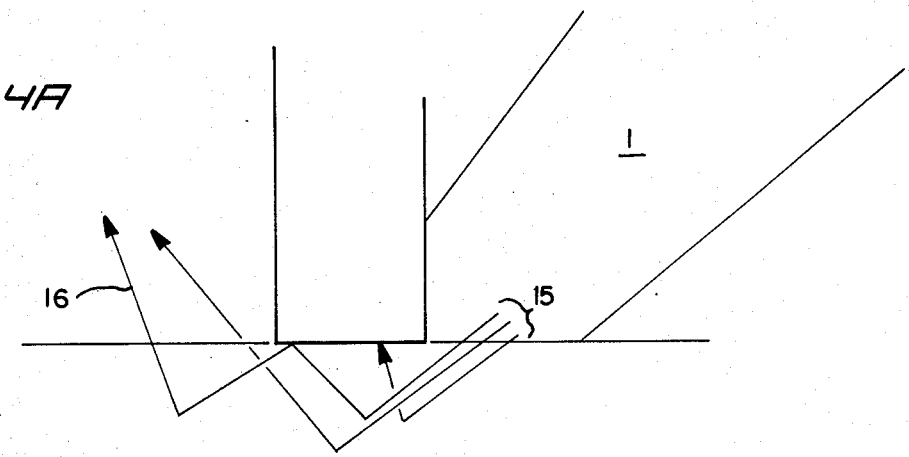
FIGS. 4A and B show a cross section of an edge of a blocking element contacting the surface of the sample for use in the arrangement shown in FIG. 3.
Figure 4B:
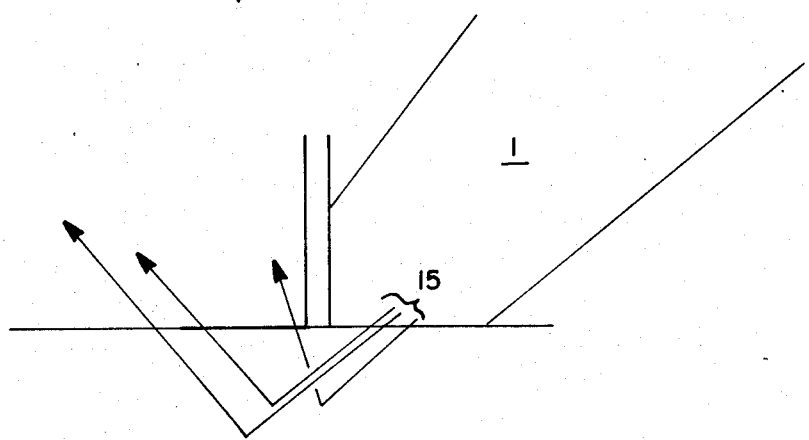

To obtain maximum efficiency and the closest approximation to the Kubelka-Munk relationship, a blocker should have an edge that is a fraction of the optical depth of the sample. Such a blade may be considered a thin blocker. A thicker blocker, by removing energy that penetrates only a short distance into the sample before reflecting, may have a catastrophic effect on efficiency when used with a sample having a shallow optical depth because input energy that penetrates to only a shallow depth may contain the majority of the energy diffused into the sample. This effect is as shown in FIG. 4A. Lines 15 represent energy rays from focused input beam 1 which penetrate the sample 5 and are diffusely reflected. As shown by this figure, only a small fraction of the energy escapes from the far side of the blocker. A thick blocker may also introduce spectral distortions caused by energy that is once reflected by the sample to the lower surface of the blocker and again reflected from the blocker to the sample before the energy escapes from the far side of the blocker as shown by line 16 in FIG. 4A. Energy thus reflected from the surface of the blocker will acquire any reflectance spectral features of the blocker itself and, thus, distort the output spectrum. Therefore, the blade edge of the blocker device should be made as thin as possible to maximize the efficiency of the device as is shown in FIG. 4B minimizing surface spectra of the blocker and permitting a great portion of the diffusively reflected energy 15 to escape from the far side of the blocker.

Figure 5A:
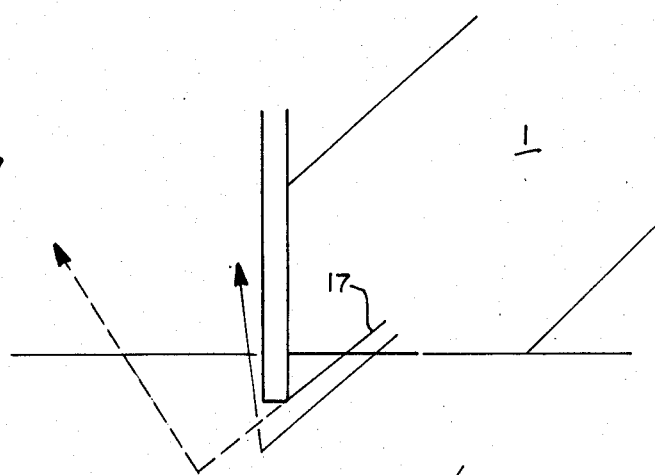
FIGS. 5A and 5B shows a cross section of a blocker blade inserted below the surface of a sample.
Figure 5B:
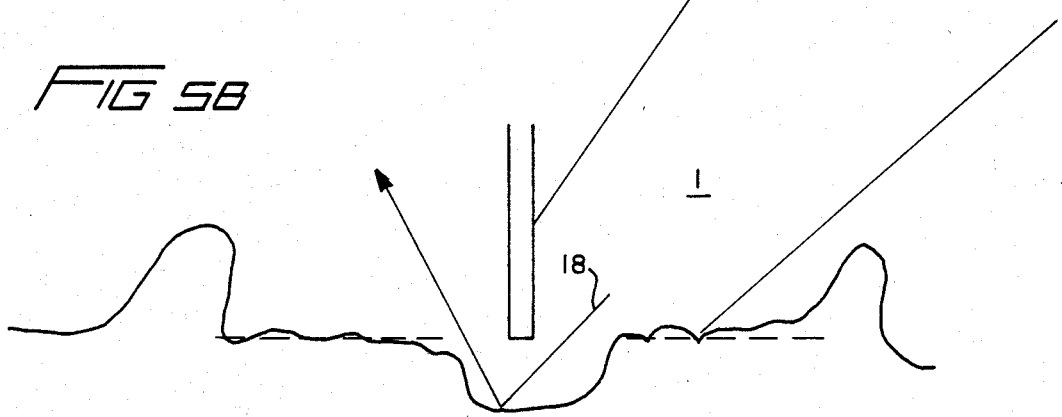

Efficiency also dictates that the blocker not penetrate the surface of the sample. As shown in FIG. 5A, penetration of the blocker into the sample blocks energy 17 that is reflected from a shallow depth and has an effect that is comparable to employing a thick blocker. In practice, however, it is sometimes necessary to break the surface of the sample with the blocker to insure that specularly reflected energy will not leak underneath the blocker at some point along the edge of the blocker as shown by ray 18 in FIG. 5B.

Figure 6A:
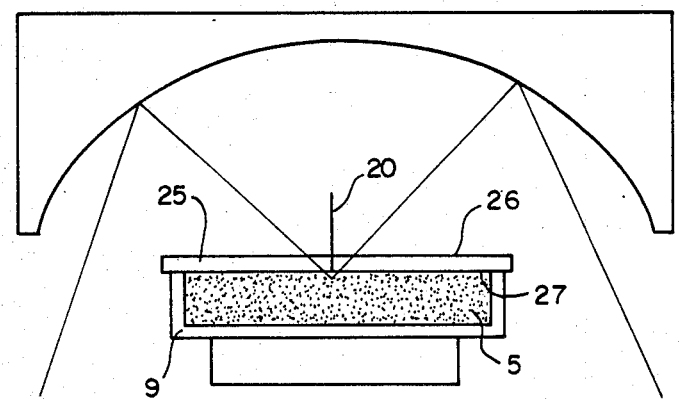
FIGS. 6A and B show an alternative embodiment of the invention.
Figure 6B:
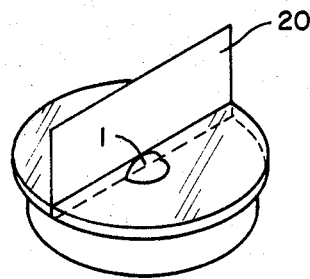

The need for penetrating the surface of a sample may be eliminated by smoothing the sample prior to moving the blocker and sample into position. One means of accomplishing this is shown in FIGS. 6A and B. The flattening window is made of transmissive material 25 having two flattened edges 26 and 27 positioned on either side adjacent to blocker 20. The window is positioned on the sample so that face 27 lightly presses or touches the surface of the sample 5 so as to smooth any surface irregularities and eliminte any leaking of specularly reflected energy under the blocker.

Figure 7A:
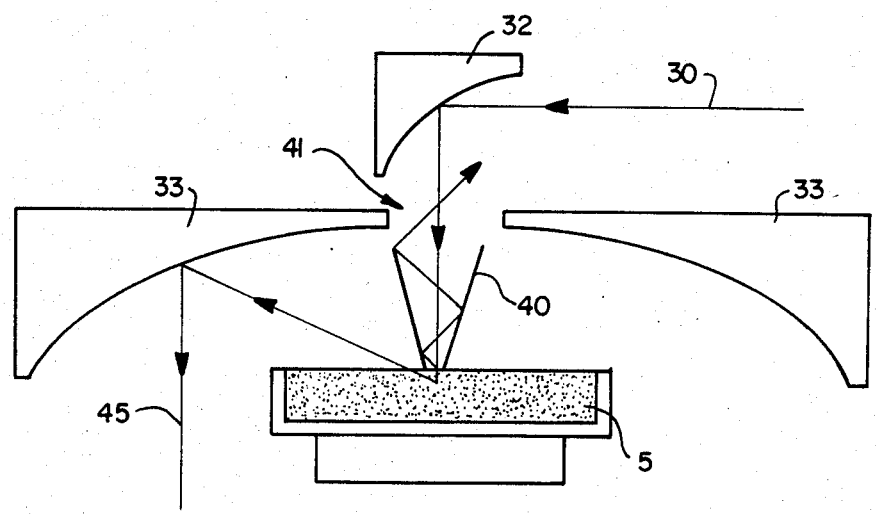
FIGS. 7A and 7B represents an alternative embodiment of the blocker shown in FIG. 3.
Figure 7B:
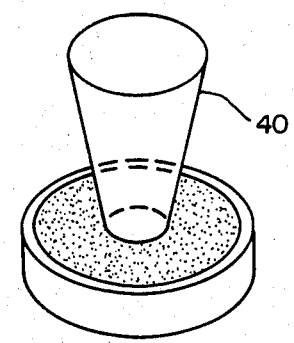

FIGS. 7A and 7B show a further embodiment of the invention. An input beam 30 is directed downward by a focusing paraboloid mirror 32 onto the sample at a substantially vertical edge. Energy penetrating the surface which is diffusively reflected exits the sample and is collected by collection mirror 33. In this embodiment, the blocker 40 assumes the shape of a cone. The tip of the cone contains an exit hole having a diameter equal to the diameter of the input beam. Specularly reflected light reflects back off the surface of the sample and exits the system by either directly reflecting back off input paraboloid mirror 32 or by multiple reflections 41 off the blocker thus removing all specularly reflected light from output beam 45.

Figure 8A:
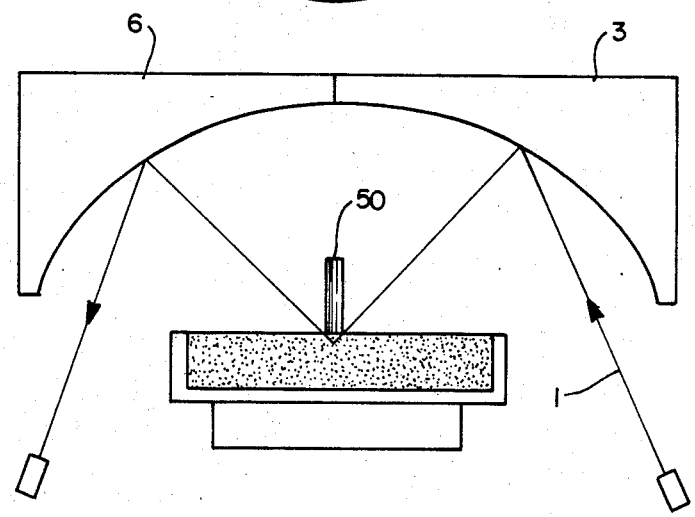
FIGS. 8A and B show a further alternative embodiment of a blocker for use in an arrangement as depicted in FIG. 3.
Figure 8B:
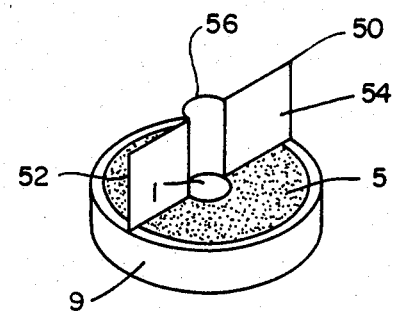

FIG. 8 shows a further embodiment of the invention. Blocker 50 has three edge surfaces. Surfaces 52 and 54 are straight edges. Surface 56 is arcuate-shaped to match the shape of the edge of the input beam when focused on the surface of the sample. The advantages to the arcuate shape will lie in potentially obtaining greater efficiency of use from the input beam in that the entire beam reaches the surface of the sample rather than having half of the beam reflected off the blocker as is the case for the blocker shown in FIG. 3.

In general, the ideal optical arrangement for the blocker device has a symmetrical design where no attempt is made to otherwise optically exclude specular energy. Therefore, all energy received by the output half of the ellipsoid mirror 6 in FIG. 1 should be directed to focus 7. The blocker has proven so effective at removing the specular component of reflected energy that no need exists to discriminate between light received by areas 10 and 12 in FIG. 2. Experiment has shown that efficiency is a major consideration in obtaining diffuse reflectance spectra using the blocker device. Some samples, particularly finely powdered samples, do not permit the input energy beam to penetrate more than a few wavelengths into the sample. A high percentage of the energy reflected from such a sample is specular. Therefore, obtaining a spectrum within a reasonable time period requires a collector to operate at maximum efficiency, and efficiency is enhanced by utilizing all energy diffusely reflected from the sample. It is also suggested that high efficiency detectors be employed to measure the resultant output.

It is believed that the blocker will result in the linearization of the output spectrum according to the Kubelka-Munk formula since present theory maintains that deviations of diffuse reflectance spectra from the Kubelka-Munk relationship are produced solely or primarily by specular reflection.

Figure 9:
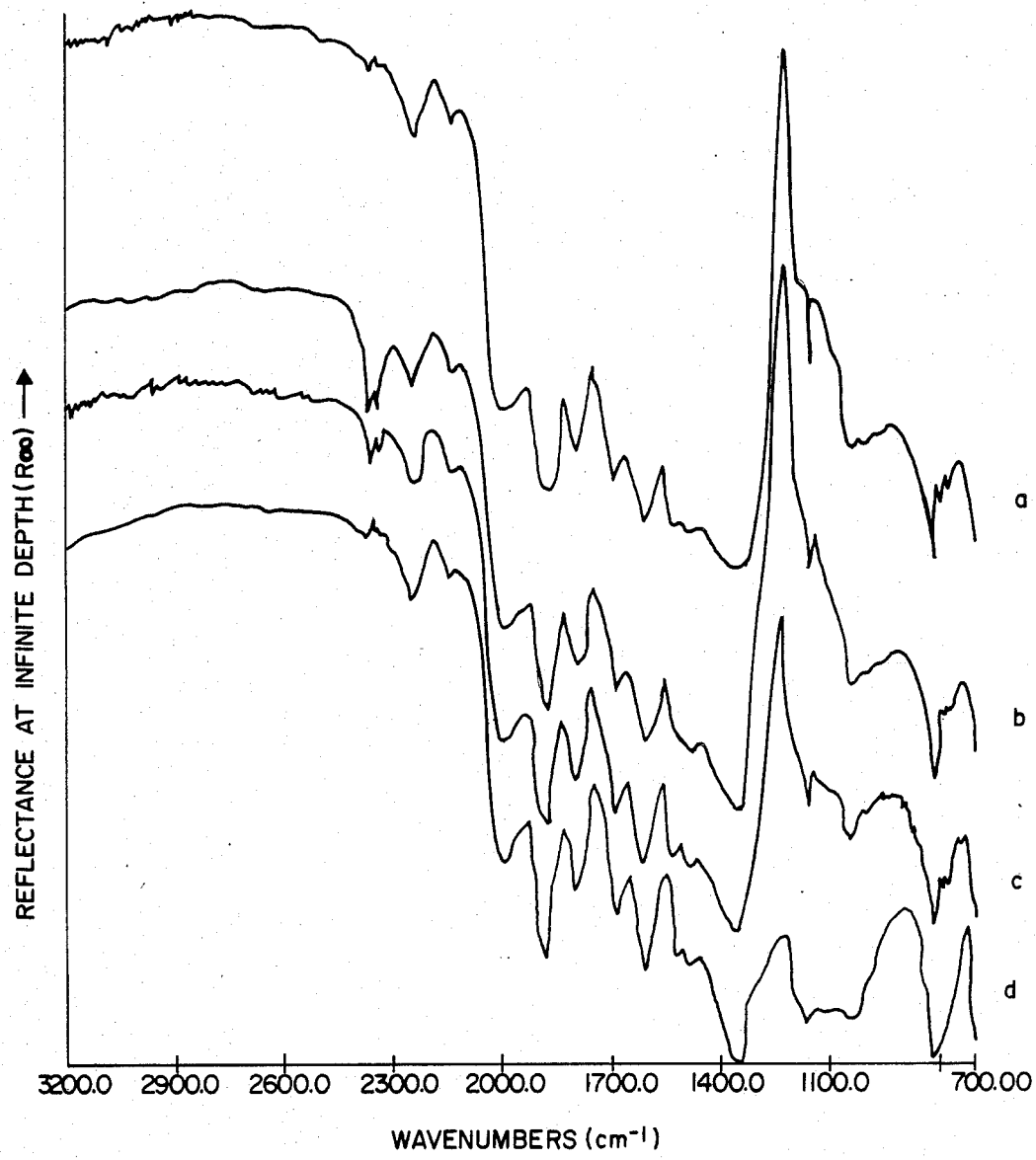
FIGS. 9 and 10 show comparison spectra from ground sand showing how the distortions caused by specular reflection are eliminated through using the blocker of the invention.

FIGS. 9–14 are comparisons of infrared diffuse reflectance spectra for various materials obtained with and without the blocker of FIG. 3. FIG. 9 is a comparison of an infrared spectrum of neat, ground sand obtained by diffuse reflectance. Curve a is a measure of the spectrum obtained without a blocker device using the entire output half of the ellipsoid mirror 6 of FIG. 2. Curve b is a spectrum obtained by masking region 10 of the ellipsoid mirror 6. Curve c is the spectrum produced when region 12 is masked. Specular distortion of the diffuse reflectance spectrum is present in all three cases. Curve d shows that a dramatic reduction in the specular reflectance can be obtained by roughening the surface of the sample.

Figure 10:
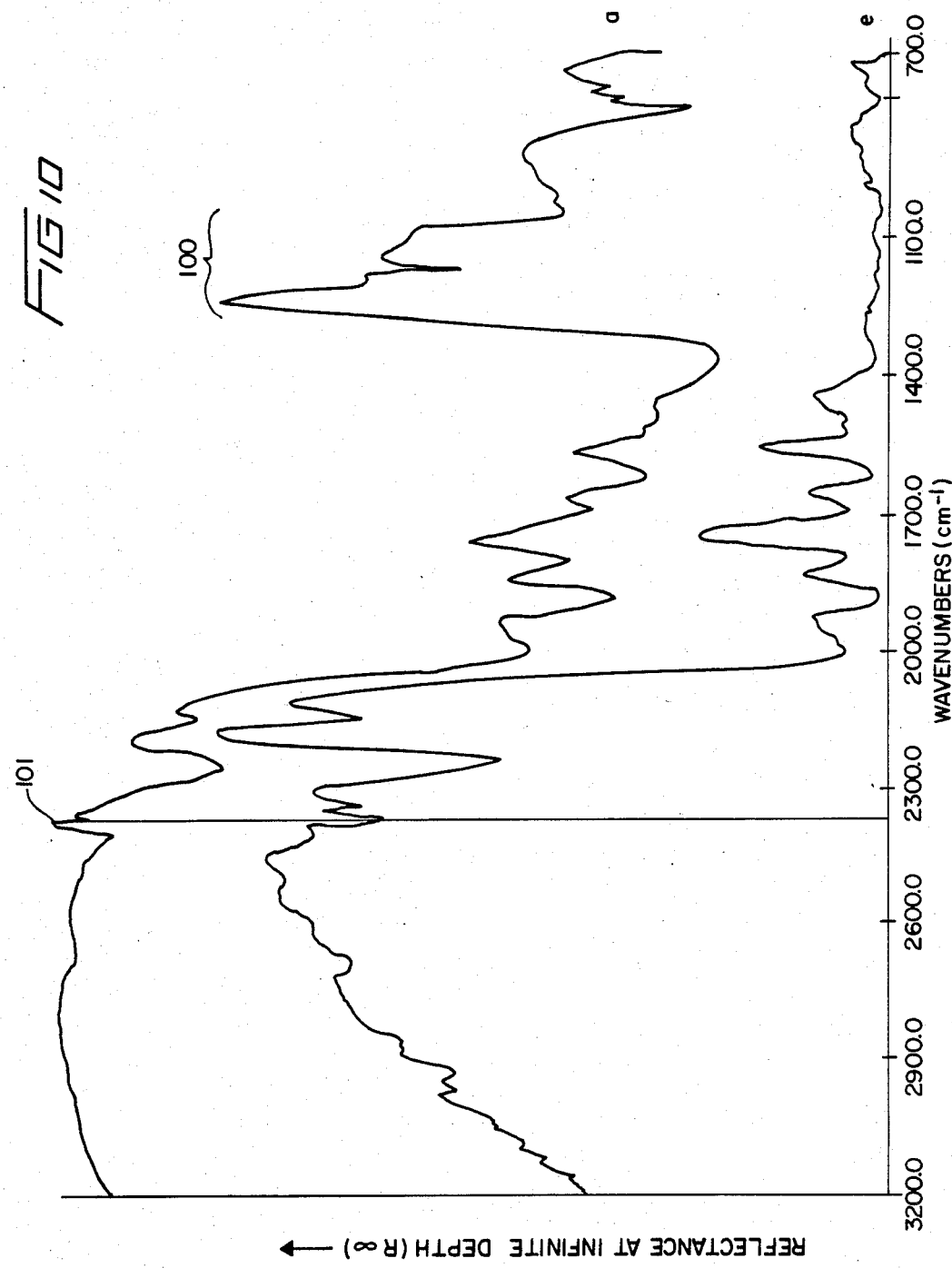

FIG. 10 shows a comparison between curve a of FIG. 9, i.e., the diffuse spectrum employing the full output half of the ellipsoid mirror 6, and a diffuse spectrum e obtained using the blocker device. Curve d in FIG. 9 obtained by roughening the surface produces markedly less specular distortion. However, spectrum e of FIG. 10 contains substantially less specular distortion than even curve d. This effect is most noticeable by comparing the peak value of the spectral feature labelled generally 100. Spectral feature 100 is pronounced in curve a containing the highest specular component. Even curve d contains some element of this distortion. Spectral feature 100 is completely absent in curve e.

Thus, spectral feature 100 is an example of the nature of the distortion introduced into a diffuse reflectance spectrum by specular reflection. Note that in FIG. 10 spectral feature 101 appears to be an example of a band inversion or reststrahlen band.

Figure 11:
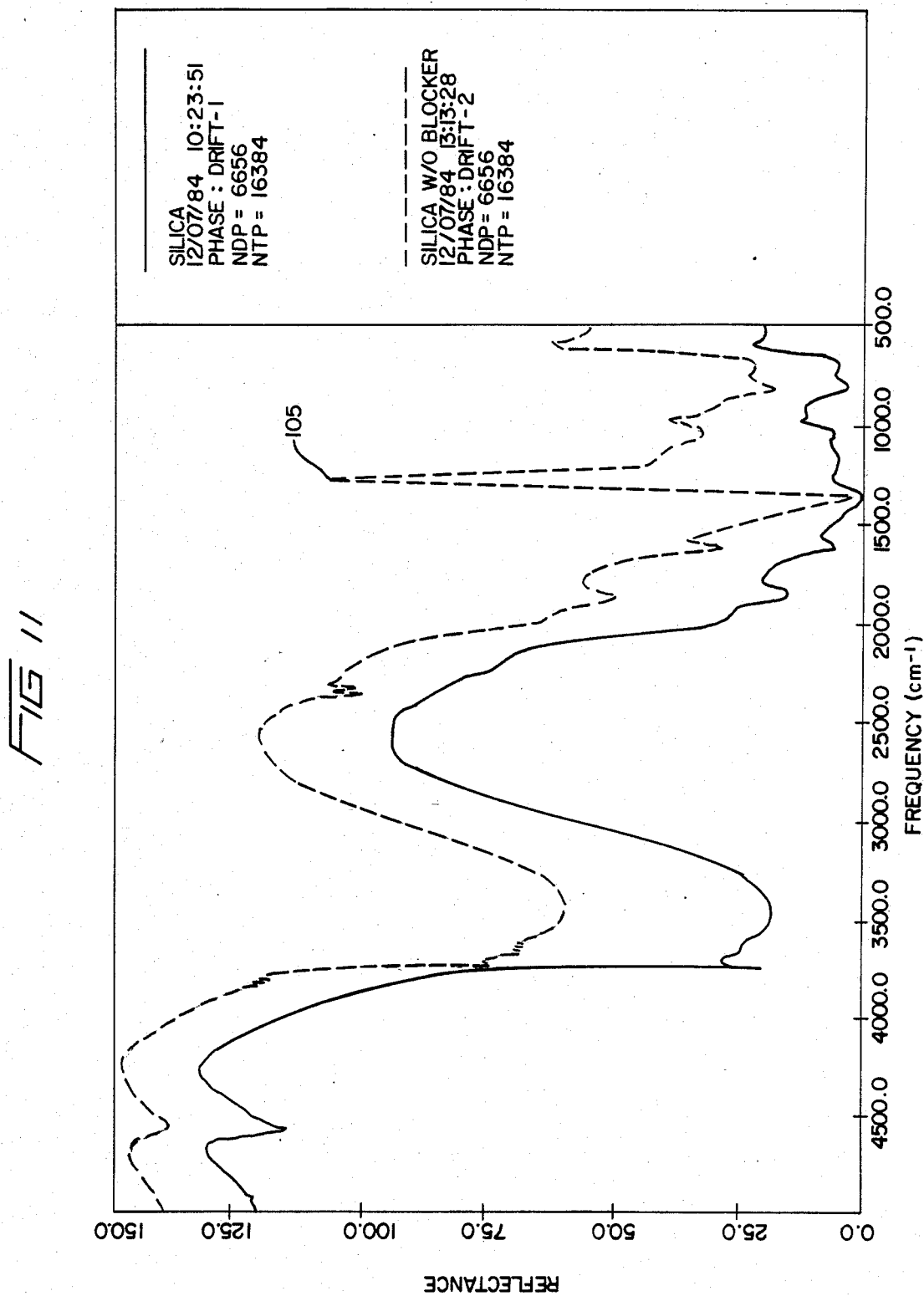
FIG. 11 provides a comparison of diffusive spectra obtained from silica demonstrating the effect of the blocker according to the present invention at reducing the specular component of diffusive spectra.

FIG. 11 shows another infrared comparison spectrum of silica. The upper line shows the spectrum having a specular component. The lower spectrum shows the spectrum obtained with the use of the blocker. Note again how spectrum feature 105 totally disappears with the use of the blocker device.

Figure 12:
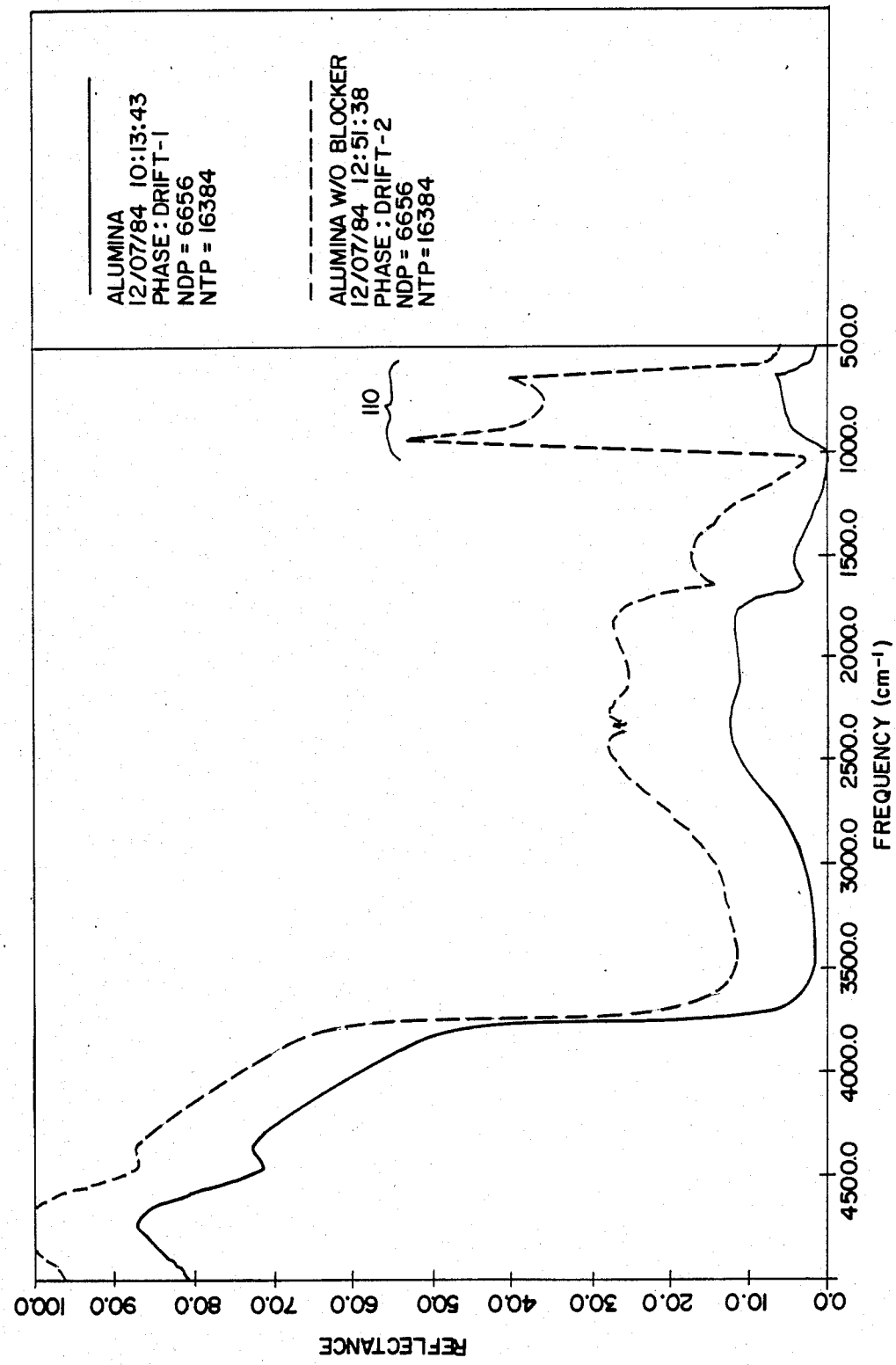
FIG. 12 shows a similar comparison to FIG. 11 for alumina powder.

Similarly, FIG. 12 shows comparison spectra for alumina. Note how specular reflectance feature 110 disappears in the diffuse reflectance spectra obtained with the blocker device.

Figure 13:
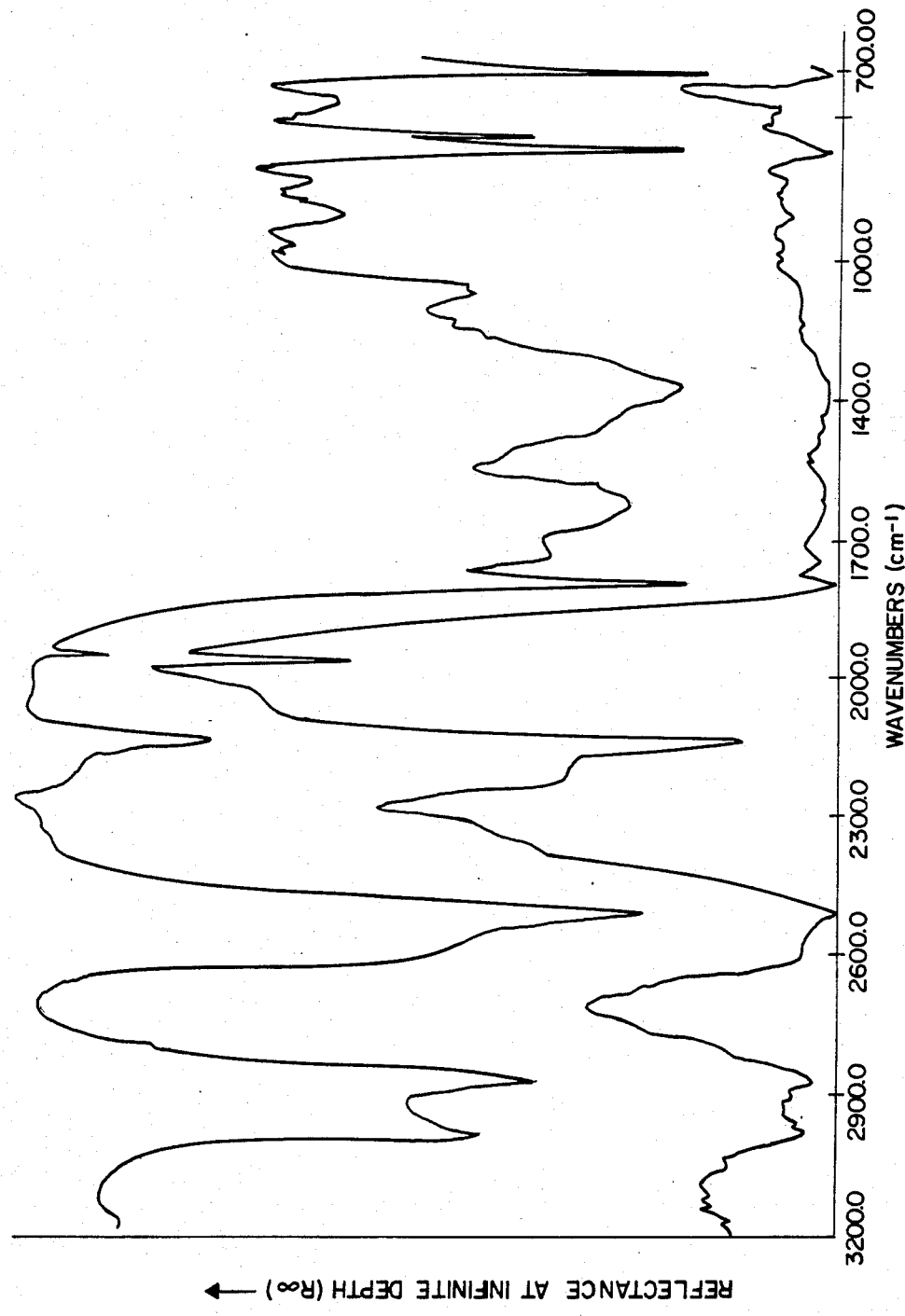
FIG. 13 shows a spectrum similar to FIG. 11 for finely powdered calcite.

FIG. 13 shows comparison diffuse reflectance spectra for finely powdered calcite. The energy distribution across wavelengths between the two spectra is clearly different The foregoing figures illustrate the ubiquitous presence of specular reflection distortion in infrared diffuse reflectance spectroscopy and how this distortion can be eliminated through use of the blocker device.

Not all diffusely reflecting compounds produce specular distortion. FIG. 14 is a comparison spectrum of ethylanthroquinone. This solution, as is true for most organic compounds, does not exhibit spectral distortions caused by specular reflection due to the absence of strong resonance bands at infrared frequencies. Thus, the blocker does not significantly change the spectrum obtained through unblocked diffuse reflectance spectroscopy.

Operation of the blocker device according to the present invention has been described by way of example as applied to infrared spectroscopy. As noted, the blocker has particular utility in the field of infrared diffuse reflectance spectroscopy of inorganic compounds. However, the foregoing specification enables one of ordinary skill in the art to apply the principles of the blocker device to any instance where an energy beam consisting of a particle demonstrating significant quantum mechanical wave properties is incident on the surface of a material that reflects the incident beam at both the surface of the material and from below the surface. Therefore, the invention which is intended to be protected herein should not be construed as limited to the particular forms described, as these are to be regarded as illustrative rather than restrictive. Variations and changes may be made by those skilled in the art without departing from the spirit of the present invention. Accordingly, the foregoing detailed description should be considered exemplary in nature and not as limiting to the scope and spirit of the invention as set forth in the appended claims.

What we claim is:

1. An apparatus for obtaining a diffuse reflectance spectra comprising:
   means for providing an incident energy beam;
   means for directing the incident energy beam to a sample;
   means for collecting energy that is diffusely reflected from the sample;
   blocking means positioned on or adjacent to the sample to substantially eliminate energy that is specularly reflected off the sample.
2. The apparatus of claim 1, wherein
   the means for providing an incident energy beam to the sample includes means for focusing the incident energy beam substantially at a surface of the sample; and the means for collecting the energy that is diffusely reflected from the sample includes means for focusing the reflected energy onto a detector means.

3. The apparatus of claim 2, wherein
the incident energy beam contains infrared radiation; and
the detector is used for obtaining a diffuse reflectance spectrum of the sample.

4. The apparatus of claim 2, wherein the blocking means on or adjacent to the sample does not penetrate the surface of the sample.

5. The apparatus of claim 2, wherein said blocking means is separated from a surface of the sample by a distance that is less than a wavelength of the energy of the incident energy beam.

6. The apparatus of claim 2, wherein said blocking means has a thickness that is not substantially greater than the average penetration of the incident energy beam into the sample.

7. The apparatus of claim 2, wherein said blocking means is a straight-edged object that extends substantially beyond edges of the incident energy beam.

8. The apparatus of claim 2, wherein
said blocking means is generally conical in shape; and
the means for directing the incident energy beam to the sample is positioned such that the incident energy impinges substantially normal to the sample through an aperture in the blocking means.

9. The apparatus of claim 2, wherein the blocking means is arcuate-shaped to substantially match an outer edge of at least one-half of a shape of the incident energy beam on the surface of the sample.

10. An apparatus responsive to a distribution of energy in a reflectance spectra, comprising
means for directing an incident energy beam to a sample;
means for receiving energy reflected from the sample; and
blocking means positioned on or adjacent to the sample to block out energy specularly reflected off the sample.

11. The apparatus of claim 10, wherein
the means for receiving and responding to energy reflected from the sample includes detector means;
the detector means receives energy containing the reflectance spectra of the sample and the sample specularly reflects energy which produces distortion of the distribution of energy in the reflectance spectra of the sample; and
the blocking means substantially eliminates the distortion in the reflectance spectra received by the detector means by blocking out the energy specularly reflected off the sample.

12. The apparatus of claim 11, wherein
the blocking means is at a distance from the sample such that the specularly reflected energy from the sample is substantially eliminated without also substantially eliminating energy from the sample which is not specularly reflected; and
the detector means is used in obtaining a diffuse reflectance spectra from at least a portion of the energy not specularly reflected from the sample.

13. The apparatus of claim 11, wherein the substantial elimination of the distortion in the reflectance spectra received by the detector causes at least a portion of the energy in the spectra to vary linearly with a concentration of a composition of matter in the sample producing the absorption feature.

14. The apparatus of claim 11, wherein the substantial elimination of the distortion in the reflectance spectra received by the detector produces a reproducible spectra of the sample that is indicative of a composition of or a concentration of a substance contained in the sample.

15. A method for blocking out specularly reflected energy, comprising
directing energy to a sample;
positioning a blocking element on or adjacent to the sample so that the specularly reflected energy from a surface of the sample is separated from energy diffusely reflected from the sample;
collecting the energy diffusely reflected from the sample.

16. The method of claim 15, wherein
the directing of the energy to the sample comprises focusing a beam of energy onto the surface of the sample;
the positioning of the blocking element includes positioning an edge of the blocking element at a distance from the surface of the sample not substantially greater than a wavelength of the energy;
the collecting of the diffusely reflected energy includes focusing the diffusely reflected energy to a detector.

17. The method of claim 16, wherein the detector is used to obtain a diffuse reflectance spectrum of the sample.

18. The method of claim 17, wherein the energy is at infrared wavelengths.

19. The method of claim 16, wherein the positioning of the blocking element on or adjacent to the surface of the sample does not cause the edge of the blocking element to penetrate into the sample.

20. The method of claim 16, wherein
the positioning of the blocking element is determined by a predetermined positioning of the collecting means; and
the positioning of the collecting means determines a positioning of the sample.

* * * * *

Disclaimer and Dedication 4,661,706—Robert G. Messerschmidt, Westport; Donald W. Sting, New Canaan, both of Conn. BLOCKER DEVICE FOR ELIMINATING SPECULAR REFLECTANCE FROM A DIFFUSE REFLECTION SPECTRUM. Patent dated April 28, 1987. Disclaimer and Dedication filed June 11, 2001, by the assignee, Spectra-Tech. Inc.

Hereby disclaims and dedicates to the Public all claims and entire term of said patent.
*(Official Gazette, July 31, 2001)*